United States Patent [19]

Sulitzeanu

[11] Patent Number: 4,508,829

[45] Date of Patent: Apr. 2, 1985

[54] METHOD AND KIT FOR PREGNANCY DETECTION

[75] Inventor: Bernard Sulitzeanu, Jerusalem, Israel

[73] Assignee: Teva Pharmaceutical Industries Ltd., Israel

[21] Appl. No.: 409,053

[22] Filed: Aug. 18, 1982

[30] Foreign Application Priority Data

Sep. 16, 1981 [IL] Israel ......................................... 63855

[51] Int. Cl.³ ...................... G01N 33/54; G01N 33/58; G01N 33/76
[52] U.S. Cl. ...................................... 436/510; 422/61; 436/65; 436/519; 436/808; 436/814; 436/818; 436/827
[58] Field of Search ............... 436/827, 510, 519, 808, 436/814, 818, 65; 422/61

[56] References Cited

U.S. PATENT DOCUMENTS

| | | | |
|---|---|---|---|
| 4,105,598 | 8/1978 | Yen et al. | 521/53 |
| 4,190,628 | 2/1980 | Sears | 422/61 |
| 4,289,747 | 9/1981 | Chu | 424/1 |
| 4,302,536 | 11/1981 | Longenecker | 436/801 X |
| 4,371,515 | 2/1983 | Chu | 436/827 X |
| 4,419,453 | 12/1983 | Dorman | 436/510 X |

FOREIGN PATENT DOCUMENTS

| | | |
|---|---|---|
| 0014965 | 2/1980 | European Pat. Off. |
| 47223 | 1/1979 | Israel . |
| 48741 | 7/1979 | Israel . |
| 50929 | 11/1980 | Israel . |
| 1561920 | 3/1980 | United Kingdom . |

OTHER PUBLICATIONS

P. G. Natali et al., Jour. of Immunological Methods, 25, 255–264, (1979).
Koyama et al., Folia Endocrinol. Jap. 55, 1979, pp. 133–140, (Abstract in English).
Braciale et al., Journal of Immunological Methods, 43, (1981), pp. 241–250.
Pompecki et al., Cancer Research, 41 (1), (1981), pp. 1905–1909.
Guesdon et al., Journal of Immunological Methods, 39, (1980), pp. 1–13.

*Primary Examiner*—Sidney Marantz
*Attorney, Agent, or Firm*—Steinberg & Raskin

[57] ABSTRACT

Method and kit for pregnancy detection adapted for self-performance. Urine to be tested is contacted with a lectin substrate being lectin bound to a solid support and capable of binding HCG. After separation of the lectin substrate from the urine the substrate is contacted with a liquid color reagent comprising a colored carrier material and anti-HCG antibodies bound thereto. If after separation of the colored reagent from the substrate the latter remains colored, the subject is pregnant, while lack of color indicates non-pregnancy. A preferred color reagent comprises killed and stained Staphylococci bacteria. There is also provided a kit for self-performance of the method comprising at least one column packed with a lectin substrate and adapted for the controlled passage of liquid therethrough, and a color reagent.

14 Claims, 1 Drawing Figure

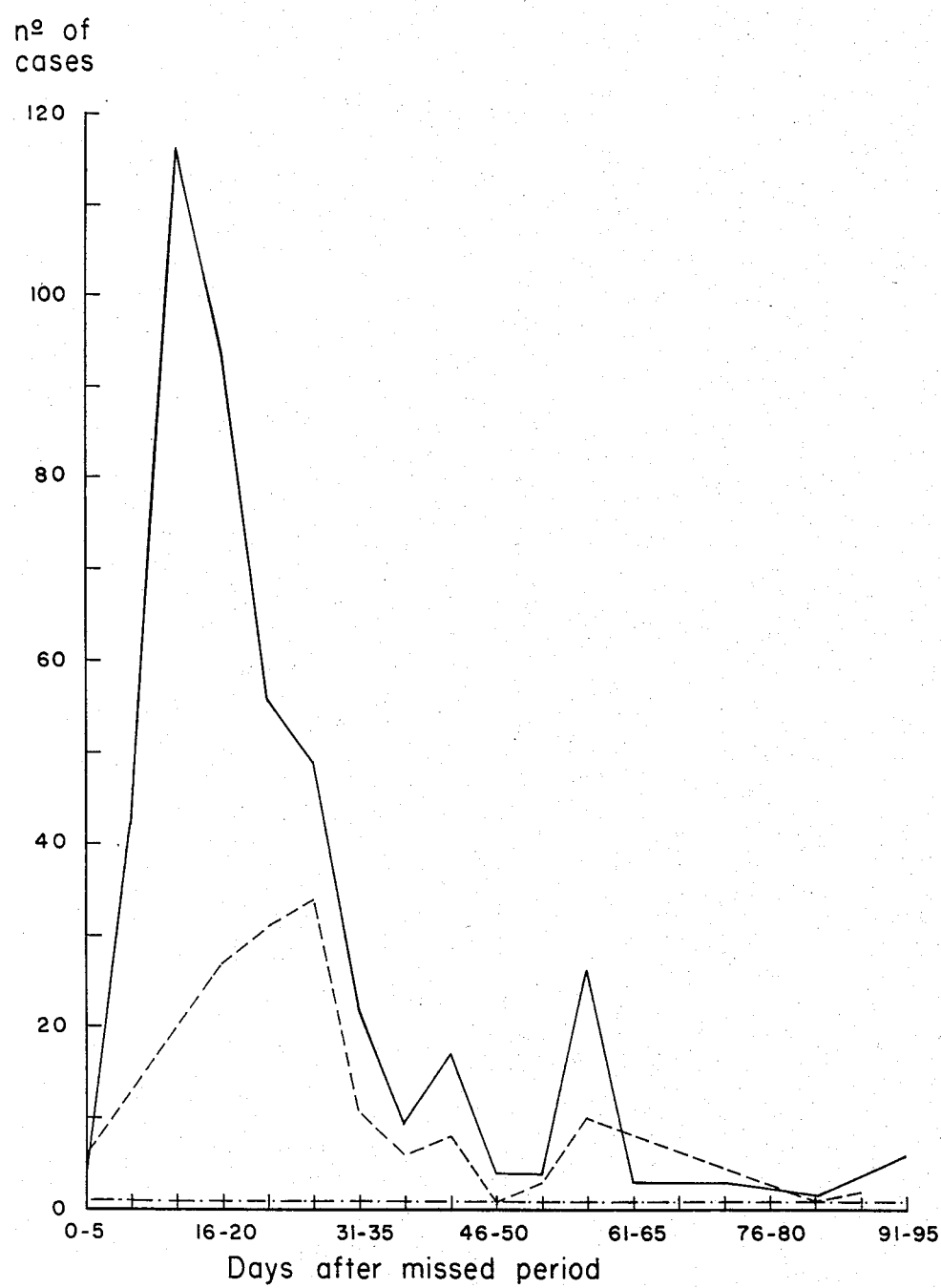

METHOD AND KIT FOR PREGNANCY DETECTION

BACKGROUND OF THE INVENTION

The present invention concerns a method and a kit for early pregnancy detection.

Pregnant women secrete soon after the implantation of a fertilized ovum in the chorionic tissues an increasing amount of human chorionic gonadotropin (HCG) some of which is excreted in the urine. Most presently available pregnancy detection methods are based on the detection of HCG in the urine.

One group of known methods for the detection of HCG in the urine is based on radioimmunoassay. While these methods are very reliable and sensitive they require highly sophisticated laboratory equipment and such tests cannot be carried out by the subjects themselves.

Another group of tests known as enzyme linked immunosorbents assay (ELISA) is based on an enzymatic reaction associated with HCG as described, for example, in Israel patent specification No. 48741 (Rafa Laboratories). In accordance with that method a solution of an anti-HCG antibody labelled with an enzyme is mixed with a urine sample to be tested. The mixture obtained is then mixed with anti-HCG antibody associated with a carrier. In the absence of HCG in the urine, subsequent washings and centrifugations of the substrate will remove the anti-HCG antibody with the enzyme linked thereto. Accordingly, addition to the residue remaining in the vessel of a non-coloured solution capable of developing a colour in the presence of the enzyme will in this case not give rise to the development of any colour. If, however, HCG is present the enzyme will be retained in the residue. In that case the addition of the said solution will give rise to the development of a colour.

This and similar methods have however not been commercialised, apparently for the reason that they are not sufficiently sensitive and reliable.

Another group of known methods is based on agglutination that occurs upon reaction of anti-HCG antibodies adsorbed on a carrier such as latex particles, and HCG present in the test fluid, or the prevention of agglutination of HCG sensitized latex particles or red cells. In the direct, agglutination method anti-HCG antibody bearing material is contacted with the tested urine and if the latter contains HCG there occurs an agglutination which can be detected visually. In accordance with the indirect, agglutination inhibition method anti-HCG antibodies are contacted with the tested urine and subsequently with a reagent comprising HCG deposited on gel particles or on red blood cells. If the urine contains HCG the latter reacts with the anti-HCG antibodies with the consequence that the subsequently added HCG reagent does not cause agglutination. If, however, the tested urine does not contain any HCG the anti-HCG and HCG reagent react with each other with consequential agglutination.

Such methods are described, for example, in European patent application No. 0014965 (Hoffmann-La Roche), U.K. patent No. 1,561,920 (Warner Laboratories), Israel patent No. 50929 (American Home Products Corporation) and Israel patent No. 47223 (Rafa Laboratories).

Some of these methods have become commercial and are even used for do-it-yourself testing. However, these methods have some drawbacks in that they are of limited sensitivity, not sufficiently reliable in that they produce a relatively high proportion of false positive and false negative results, and cannot be employed in the very early stages of pregnancy.

The early and reliable detection of pregnancy is of great importance. Thus, where for some reason the pregnancy is undesired and has to be interrupted it is important to establish the pregnancy in as early a stage as possible. In other cases, where the woman is in the habit of taking certain drugs which may be teratogenic, it is important to know of the pregnancy as early as possible so that the taking of such drugs may be interrupted. In still other cases where it is known that the woman will suffer from certain ailments in consequence of pregnancy, e.g. an inability to hold the fetus under normal conditions, adequate treatment has to be initiated as soon as possible.

As a rule women are reluctant to go to laboratories for testing at an early stage of a missed period, be it because of the trouble that this involves or be it for psychological reasons.

SUMMARY OF THE INVENTION

For all these reasons it is of great importance to provide a simple and reliable method for the earliest possible self-determination of pregnancy. It is the object of the present invention to provide such a method and a kit therefor.

In accordance with the present invention there is provided a method for the detection of pregnancy comprising:

(i) contacting urine of a tested subject with a lectin bound to a solid support (lectin substrate) and capable of binding HCG;

(ii) separating the lectin substrate from the urine;

(iii) contacting the lectin substrate with a liquid reagent comprising a coloured carrier material and anti-HCG antibodies bound thereto (colour reagent); and (iv) separating the colour reagent from the lectin substrate.

The liquid colour reagent will as a rule be in form of an aqueous suspension.

During the contact between the lectin substrate and the tested urine any HCG present in the urine is bound by the lectin. During the subsequent contact between the lectin and said colour reagent, the anti-HCG antibodies react with any HCG bound to the lectin with the conseqence that the coloured carrier is also bound to the lectin. Accordingly, if HCG was present in the tested urine then after the separation of the excess colour reagent from the lectin, the lectin substrate remains stained. If on the other hand, no HCG was present in the tested urine none of the colour reagent is bound to the lectin so that after separation from the colour reagent the lectin substrate remains unstained.

DETAILED DESCRIPTION OF PREFERRED EMBODIMENTS

Thus stained lectin substrate at the end of the test signifies pregnancy while unstained lectin substrate at the end of the test signifies non-pregnancy.

A typical lectin that can be employed in accordance with the invention is Concanavalin A (hereinafter for short Con-A) which is a lectin extracted from the meal of Jack bean.

Example of other lectins that can be employed in accordance with the invention are wheat germ lectin, lentil lectin and soy bean lectin.

In the performance of the new method according to the invention HCG is adsorbed by the lectin substrate and accumulates thereon and in this way HCG from a relatively large amount of urine is concentrated in a simple and effective way. Consequently a relatively large amount of HCG is subsequently brought into reaction with the anti-HCG antibody and in this way the sensitivity of detection is increased several fold as compared to commercially available, non-isotopic techniques.

A significant innovation and departure that characterizes the invention is the use of a pre-stained colour reagent and the absence of any in-situ colour reaction. Consequently the presence or absence of HCG in the tested urine can be read unmistakably with the naked eye by the presence or absence of colour on the lectin substrate.

In a preferred embodiment of the invention the colour reagent comprises killed and stained Staphylococci bacteria of the kind that when alive produces protein A, coated with anti-HCG antibodies. Some Staphylococci bacteria produce protein A which is capable of binding immunoglobulins, including anti-HCG antibodies, and this protein remains present in the killed bacteria.

Because of their content of protein A and the ability of that protein to interact with immunoglobulins (IgGs), Staphylococci bacteria are widely used as an immunological reagent. Thus, protein A binds with very high affinity ($2 \times 10^8$ 1/mole) to over 90% of the IgG of rabbits, humans and guinea pigs and to a lesser extent to the IgGs of Mice, rats and other species. Binding of protein A to IgG is extremely rapid being complete in a matter of seconds. These properties have been taken advantage of by the use of Staphylococci in immunoassays, for direct binding of primary immune complexes instead of the second antibody (see for example, Natali et al, Journal of Immunological Methods, 25 (1979), 255–264). Use is being made of these properties of Staphylococci bacteria for the purposes of the present invention in a manner that has never been suggested before.

Alternatively it is also possible to bind the anti-HCG antibodies with other suitable carriers such as, for example, coloured latex. However, in such cases it is necessary to perform more complicated reactions for binding the anti-HCG antibodies to the carrier and care must be taken that such reaction do not adversely affect the antibody.

Examples of solid supports for the lectin are various gels such as the bead-formed agarose gel Sepharose. For example, Con-A covalently bound to Sepharose 4B (8–10 mg Con-A per 1 ml packed gel), produced by Pharmacia Fine Chemicals, Sweden, can be used. A similar preparation can be obtained by coupling Con-A to Br-CN activated Sepharose B as described extensively in the literature.

In a preferred embodiment of the invention the lectin substrate is packed into a column adapted for the controlled passage of liquids therethrough. In the performance of the method with such a column the urine is loaded onto the column and is then discharged. Thereafter the colour reagent is passed through the column and this is followed by washing with a suitable buffer solution. If at the end of the operation the column remains stained the test result is positive, i.e. the subject is pregnant. If, on the other hand, the column remains unstained the test result is negative, i.e. the subject is not pregnant.

The invention also provides a kit for the selfperformance of the pregnancy detection method according to the invention, which kit comprises at least one column packed with a lectin substrate and adapted for the controlled passage of liquid therethrough, and a colour reagent (as herein defined).

Preferably the kit according to the invention also contains means such as a funnel and filter paper for the introduction of the test urine into the column.

Preferably the anti-HCG antibody colour reagent is packed in unit dosage form such that each such dosage is suitable for the performance of one single test.

The kit according to this invention may also contain a buffer solution for washing the column prior to final reading.

The anti-HCG colour reagent may be supplied in liquid form, e.g. as a suspension in a buffer solution or in a lyophilized form together with a separately packed buffer solution. In the latter case the required colour reagent suspension is prepared before carrying out the test.

Preferably the kit according to the invention also contains instructions for the performance of the pregnancy test according to the invention.

The pregnancy testing method according to the invention is sensitive, reliable and simple to perform and gives reliable results already at a very early stage of pregnancy, as early as 6 days after a missed period. The false positive results have been found to be less than 1% while there are practically no false negative results. The sensitivity of the test is high and less than 1 IU/ml of HCG in the urine can reliably be detected. The results are obtained very fast, e.g. within 10–20 minutes from start to finish as compared to at least 2 hours in the known hemaglutination test.

Also the test according to the invention is not affected by vibration and other external disturbances which compares favourably with the hemaglutination tests that are affected even by unnoticed vibrations.

The results obtained in accordance with the invention are illustrated in the accompanying drawing which contains graphical representations of the test results obtained from the urine of 690 out of 963 tested subjects (for the balance of 303 subjects the exact day after the missed period could not be determined). The graphs represent the number of tests as a function of days after a missed period. The drawn out line represents positive test results, the dotted line negative test results and the dash-dotted line false positive results. There are no false negative results.

A typical kit according to the invention comprises the following components:
  A transparent stoppered plastic column which contains 1.5 ml of Con-A Sepharose 4B admixed with pure Sepharose 4B, the mixture having been washed with a solution of ovalbumin;
  Filter paper;
  An ampoulle containing 2 ml of acetate buffer;
  An ampoulle containing 500 µl of a colour reagent as in Example 5 hereinafter.

The procedure of performing a test with this kit is as follows:

The stoppers at the upper and lower ends of the column are opened to let the fluid that is in the column drip out until just before drying. Three ml of first morning urine is loaded onto the column through the opening containing a filter paper and allowed to drip out until just before drying. Then the colour reagent is loaded onto the column. This is followed by washing with 2 ml of acetate buffer and then the results are read: If the column is stained the test is positive, i.e. the subject is pregnant. If the column remains white the test is negative, i.e. the subject is not pregnant.

The preparation of the various components of the kit according to the invention will now be described by way of example only:

EXAMPLE 1

PREPARATION OF THE COLUMN

A batch of gel for packing the column is prepared by mixing 1 volume of a 50% suspension of Con-A Sepharose 4B, 1.5 volumes of a 50% suspension of Sepharose 4B and 1.25 volumes of acetate buffer pH 6.0, and the mixture is degased in vacuo. 3 ml of the degased mixture are loaded onto a column whose lower, discharge end is stoppered. The column dimensions are 8×1 cm. The column is placed in vertical position and the mixture therein is allowed to set for 1 hour at room temperature. Thereafter the column is washed with 10 ml of acetate buffer pH 6.0 containing 1.0% of sodium azide and 0.05% of a surfactant known commercially as "Tween 20" (trade mark). There follows another washing with 3 ml of an aqueous solution of 2 mg/ml of ovalbumin. The column is then stoppered below and on top with some liquid remaining inside so as to cover the upper surface of the gel.

EXAMPLE 2

PREPARATION OF KILLED STAPHYLOCOCCI

Staphylococcus aureus strain 12598 are grown according to the method described by Kessler et al (J. Immunol. 117. 1482 (1976)) on Pennasay broth containing $\beta$-glycerophosphate. The bacteria are killed by 1.5 hours fixation in 1.5% formaldehyde followed by heating to 80° C. for 5 minutes. The killed bacteria are tested for sterility and only those batches with undetected growth are used.

EXAMPLE 3

STAINING OF THE KILLED STAPHYLOCOCCI BACTERIA

The killed bacteria are stained with Hematoxylin. 2 ml of wet packed bacteria are washed in borate saline solution and resuspended in 94 ml of distilled water. One ml of 1% solution of $FeSO_4.7H_2O$ and 5 ml of 0.5% hematoxylin are added while stirring. The stirring is continued overnight in the cold. The bacteria are collected by centrifugation, washed several times with borate saline and once with a borate buffer saline solution containing 0.1% by weight of bovine serum albumin, 4% by weight of sucrose and 0.1% by weight of sodium azide. This is followed by homogenization in a pestle and a tube homogenizer in the same borate saline solution used above so as to obtain a 10% by weight of a blue coloured suspension.

EXAMPLE 4

PREPARATION OF ANTI-HCG ANTIBODIES (a) Immunization procedure

Rabbits of either sex are immunized according to the method described by Voitukaitis et al, J. Clin. Endocr. 33, 988 (1971) with either purified HCG (11,000 IU/mg) or by partially purified HCG (3,000 IU.mg). The rabbits are boosted every month until a hemagglutinating titer of at least 1:4,000 is obtained, which usually takes at least three months from the first injection. The rabbits are then bled, the serum separated and subjected to a purification process as described hereinafter.

(b) Removal of interfering antibodies (i) Preparation of polymerized normal human serum (NHS)

10 ml of NHS is admixed with 1 ml acetate buffer pH 5.0 and 3 ml of a 2.5% glutaraldehyde solution in a 0.15 M phosphate buffer solution. The mixture is stirred for 20 minutes and then left to stand for 3 hours at room temperature. The gel forming is homogenized and washed 3 times by centrifugation.

(ii) Absorption of anti-HCG antibody serum on NHS

One volume of the above pellets is admixed with one volume of the HCG antibody serum obtained in part (a) of this example and the mixture is moderately stirred for 1 hour at room temperature. This is followed by centrifugation. The partially purified supernatant serum is separated and the precipitate is discarded.

(c) Removal of Con-A binding immunoglobulins 10 volumes of the serum obtained in part (b) of this Example are mixed with one volume of Con-A Sepharose obtained from Pharmacia Fine Chemicals, Sweden, and the mixture is gently stirred for one hour. This is followed by filtering through a sintered glass filter and the eluant is collected while the precipitate is discarded.

(d) Preparation of specifically purified anti-HCG antibodies (i) Preparation of HCG immunosorbent Ultragel AcA34 (LKB) is used as the carrier. The gel is washed with water, incubated overnight at 37° C. in a 6% by volume glutaraldehyde solution in 0.1 M phosphate buffer pH 7.4 and is then washed extensively with bidistilled water.

The washed gel is incubated overnight at room temperature (or for 48 hours at 4° C.) with an equal volume of a solution of 4 mg/ml of HCG in 0.1 $\mu$ phosphate buffer, pH 7.4 At the end of the incubation the gel is washed several times with phosphate buffer saline. Columns of 5 ml immunosorbent are prepared for further use.

The gel is then washed with an eluting medium made of equal volumes of glycine-HCl buffer 0.2 M (vol/vol) pH 2.8 then again with phosphate buffer saline (PBS) and then with PBS containing 0.1% sodium azide.

The gel obtained in this way is kept in the cold and it is good for several purification cycles.

(ii) Adsorption on HCG immunosorbent

The anti-HCG antibody serum obtained under (i) above is passed twice in a very slow flow through a HCG immunosorbent column obtained in accordance with part (i). The column is washed repeatedly with phosphate buffer saline till an optical density of 0.05 or less at 280 nm is obtained in the eluant. The column is cooled in a refrigerator and washed with cold bidistilled water. The elution of the adsorbed antibodies is achieved by passing through the column in the cold 7 ml of glycine-HCl buffer of pH 2.8 containing 0.05% of bovine serum albumin, at a slow rate of flow. The eluant is neutralized immediately with an aqueous solution of tris(hydroxymethyl)aminomethane 0.2 M and NaCl 0.5 M, pH 8.5 (Tris buffer), in order to prevent the antibodies from becoming denatured by prolonged exposure to acidic condition.

This is followed by a second elution with 10–14 ml of 0.1 M HCl containing 0.05% of bovine serum albumin and 0.5 M NaCl which is again passed through the column at a slow rate of flow.

The fractions so obtained from the column are each neutralized with Tris buffer, then washed with phosphate buffer saline and kept in a phosphate buffer saline containing 0.1% by weight of sodium azide for further use.

The recovery of purified anti-HCG antibodies is from 25 to 40%.

(e) Removal of undesired antibodies by adsorption or urinary proteins immunosorbent (i) Preparation of insoluble urinary protein The commercial HCG employed in part (a) of this Example is derived from the urine of pregnant women. This urine contains also other proteinaceous material and consequently the rabbit develops also antibodies for such other material in addition to the desired HCG antibodies. Consequently a further purification is required to remove these undesired antibodies and to obtain pure anti-HCG antibodies.

For this further purification male urinary protein is used as adsorbent. This urinary protein is precipitated from whole urine by the addition of 776 g of ammonium sulfate per liter of urine while stirring for 1 hour at 4° C., followed by centrifugation at 15,000 rpm for 10 minutes. The precipitated protein is dissolved in a small quantity of phosphate buffer saline amounting to approximately 2.5% of the initial volume of urine.

The dissolved proteins are then put in a dialyzing bag and dialysis is carried out in 15 mM of phosphate buffer saline for several days in the cold with 3 daily replacements of the buffer solution. During dialysis some of the urinary proteins precipitate out.

To 0.5 ml of the insoluble urinary protein so obtained 8 ml of phosphate buffer saline containing 0.1% by volume of gluteraldehyde are added. The mixture is stirred for 1 hour at room temperature and is then centrifuged. The resultant pellets are washed twice with phosphate buffer saline and are then mixed with 7 ml of an 0.2 M aqueous glycin solution pH 8.5 and the mixture is left to stand overnight for blocking excess glutaraldehyde. The mixture is then thoroughly washed with phosphate buffer saline until the proteins are no longer detected in the washing solution. The pellets are then suspended in phosphate buffer saline at a 5% concentration.

(ii) Absorption on insoluble urinary proteins 2 ml of the purified anti-HCG antibodies obtained according to part (d) of this Example are adsorbed on 1 ml of the above urinary protein immunosorbent pellet suspension and the mixture is left to stand for 1 hour at room temperature and is then filtered on a sintered glass filter. The filtrate contains purified antibodies suitable for further use in accordance with this invention.

EXAMPLE 5

BINDING OF ANTI-HCG ANTIBODIES TO STAPHYLOCOCCI

One volume of Staphylococci bacteria killed and stained as described in Examples 2 and 3 are mixed with one volume of an appropriate titer adsorbed anti-HCG antibodies obtained in accordance with Example 4 and the mixture is left to stand for 1 minute at room temperature. The mixture is then diluted with 10–12 volumes of a borate buffer saline solution containing 0.1% bovine serum albumin, 4% by weight of sucrose and 0.1% by weight of sodium azide and the resulting mixture is the desired colour reagent according to the invention.

I claim:

1. A method for the detection of pregnancy, comprising:
   (i) contacting urine of a female subject with a lectin bound to a solid substrate, said lectin being capable of binding HCG;
   (ii) separating the solid substrate with the lectin bound thereto from the urine;
   (iii) contacting the thus-separated solid substrate with a liquid reagent comprising a carrier material of killed and stained Staphylococci bacteria suspended therein and having anti-HCG antibodies bound to said bacteria, said bacteria with anti-HCG antibodies bound thereto constituting a colour reagent; and
   (iv) separating any excess colour reagent from the lectin substrate,
      whereby any HCG in the urine will be bound to said anti-HCG antibodies bound to said bacteria to thus colour said lectin substrate, thus indicating that the subject is pregnant,
      while no HCG in the urine results in no binding of said anti-HCG antibodies to said lectin substrate and thus in no colouring of said lectin substrate, thus indicating that the subject is not pregnant.

2. A method according to claim 1 wherein the lectin is Concanavalin A.

3. A method according to claim 1 wherein the lectin is seleced from the group consisting of wheat germ lectin, lentil lectin, soy bean lectin, and mixtures thereof.

4. A method according to any one of the preceding claims wherein said solid substrate for the lectin is a gel.

5. A method according to claim 4 wherein said gel is Sepharose.

6. A method according to claim 1 wherein said colour reagent is in form of an aqueous suspension.

7. A method according to claim 1, wherein said lectin substrate is packed in a column so that liquid can pass therethrough.

8. A kit for detecting pregnancy, comprising the following separately contained components:
   (A) a colour reagent comprising a suspension in a liquid of killed and stained Staphylococci bacteria, said bacteria having bound thereto anti-HCG antibodies; and
   (B) at least one column packed with a solid substrate to which lectin is bound.

9. A kit according to claim 8 wherein the colour reagent is packed in unit dosage form.

10. A kit according to claim 8 also comprising at least one vessel with buffer solution.

11. A kit according to claim 8 wherein the said colour reagent is in form of an aqueous suspension contained in at least one vessel.

12. A kit according to claim 8 wherein the colour reagent is present in lyophilized form together with a separately packed buffer solution for the preparation of a colour reagent, in form of an aqueous suspension.

13. A kit according to claim 8 containing instructions for the performance of the pregnancy test.

14. A colour reagent for binding to HCG, to detect pregnancy, said colour reagent being in the form of a liquid suspension, and comprising
   killed and stained *Staphylococci bacteria*, and
   anti-HCG antibodies bound to said bacteria.

* * * * *